United States Patent [19]

Rogers et al.

[11] Patent Number: 5,329,810
[45] Date of Patent: Jul. 19, 1994

[54] NON-DESTRUCTIVE TEST STRIP AND METHOD FOR MEASURING PAINT FILM BUILD

[75] Inventors: Sid C. Rogers, Pendleton; Charles K. Sylvester, Anderson; Steve A. Harris, Elwood, all of Ind.

[73] Assignee: General Motors Corporation, Detroit, Mich.

[21] Appl. No.: 110,260

[22] Filed: Aug. 23, 1993

[51] Int. Cl.$^5$ .............................................. G01N 1/00
[52] U.S. Cl. .................................... 73/150 R; 73/863
[58] Field of Search ............................ 73/150 R, 863

[56] References Cited

U.S. PATENT DOCUMENTS

| | | | |
|---|---|---|---|
| 3,764,215 | 10/1973 | Wallach | 356/244 |
| 4,591,271 | 5/1986 | Byers | 356/432 |
| 4,599,562 | 7/1986 | Koch | 324/230 |
| 4,636,648 | 1/1987 | Egami et al. | 250/571 |
| 4,751,121 | 6/1988 | Kühnel et al. | 428/40 |
| 5,000,997 | 3/1991 | Ritchie et al. | 428/78 |

Primary Examiner—William A. Cuchlinski, Jr.
Assistant Examiner—Willie Morris Worth
Attorney, Agent, or Firm—A. Michael Tucker

[57] ABSTRACT

A test strip for measuring film build on a plastic piece includes a desired length of tape having an adhesive coating on an inner surface and a window. A paint strip of sufficient area to cover the window is secured to the tape by the adhesive. A backing formed from material easily peeled from the adhesive is removed when the tape is mounted on a piece prior to painting. After painting, the test strip is peeled away from the piece so that the paint strip can be separated from the tape, analyzed and stored.

8 Claims, 1 Drawing Sheet

NON-DESTRUCTIVE TEST STRIP AND METHOD FOR MEASURING PAINT FILM BUILD

BACKGROUND OF THE INVENTION

1. FIELD OF THE INVENTION

The present invention relates generally to a test strip and method for measuring paint film build particularly suited for a plastic part such as an automotive fascia.

2. DESCRIPTION OF THE RELATED ART

Soft bumper systems for both front and rear ends of automobiles are well-known. Generally, an impact bar is mounted to the frame or support structure with fasteners or other suitable means. Impact bars are designed to resist deformation during impact and reduce damage to the body and other components. Oftentimes, an energy-absorbing medium, e.g., foam or cellular units, is mounted on the outer face of an impact bar to absorb energy imparted by a collision. A fascia is fitted over the energy-absorbing medium to provide an attractive outer surface of the bumper system.

A fascia is a molded element, oftentimes formed as a pliable member in a reaction injection molding (RIM) process. After molding, a fascia can be painted a desired color. Quality checks for a painted fascia include paint thickness known as "film build". Generally film build is less than one millimeter.

Previously, film build during a production run was determined by cutting sections from various sample fascias throughout the run. The sections were analyzed and then discarded. The fascias used to provide the sample sections were scrapped.

It is desirable to determine film build of painted fascias in a manner which does not result in scrapping the fascias. Furthermore, it is desirable to preserve the film build data in an easy and economical manner.

SUMMARY OF THE INVENTION

The present invention includes a non-destructive test strip and method for determining film build on a painted fascia. The test strip is applied to the fascia prior to painting. After painting, the test strip is peeled away from the fascia. A portion of the test strip is analyzed to determine film build and easily retained in standard files. The fascia can be stripped and returned to a painting operation. In this manner, a non-destructive test strip and method are used to provide quality control checks of film build without resulting in fascia scrappage. The test strips and method can be readily adapted for other painted plastic or RIM materials.

In a preferred embodiment, a test strip for measuring film build on a plastic piece includes a desired length of tape having an adhesive coating on an inner surface and a window. A paint strip of sufficient area to cover the window is secured to the tape by the adhesive. A backing formed from material easily peeled from the adhesive is removed when the tape is mounted on a piece prior to painting. After painting, the test strip is peeled away from the piece so that the paint strip can be separated from the tape, analyzed and stored.

DETAILED DESCRIPTION OF THE PREFERRED EMBODIMENT

Figure 1:
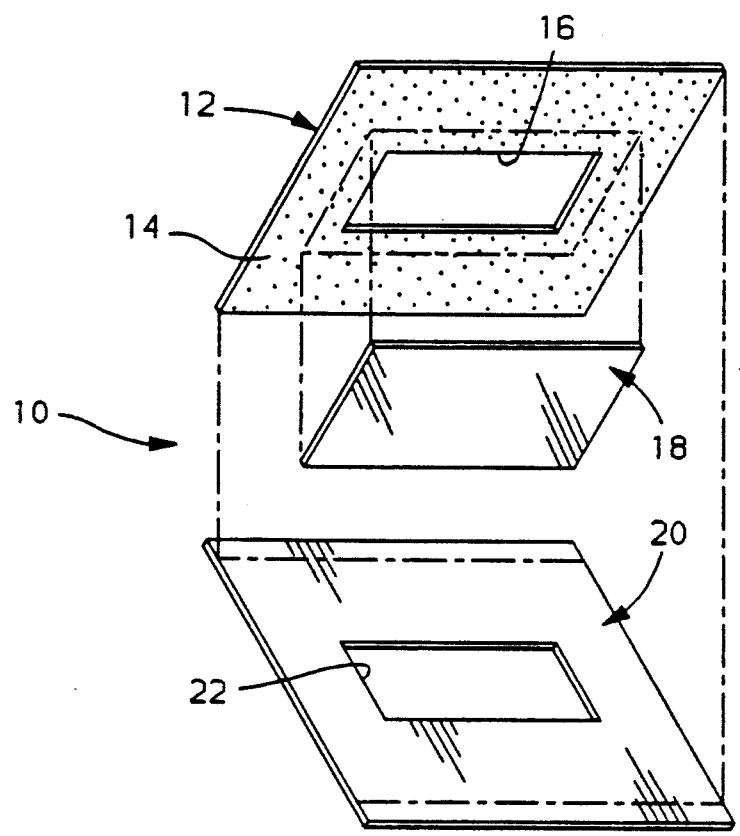
FIG. 1 is an exploded perspective view of a test strip according to the present invention illustrating a tape, a paint strip and a backing.

A test strip indicated generally at 10 in FIG. 1 is illustrated prior to application on a piece or item to be painted. The test strip 10 includes a preselected length of tape 12 having an adhesive coating on an inner surface 14 and a central cutout or window 16. In the embodiment of FIG. 1, the window 16 is illustrated as a rectangle. However, the window 16 can be of any desired shape. A paint strip 18 is held by the adhesive coating to the inner surface 14 and completely covers the window 16. Preferably the paint strip 18 has a periphery which extends beyond the area of the window 16. A backing 20 having a surface easily peeled from the adhesive coating of the inner surface 14 is held against the inner surface 14 until the test strip 10 is mounted. If desired, a complementary window 22 can be provided in the backing 20.

A series of test strips 10 can be formed in a roll for convenience. Perforations and/or cuts in the tape 12 can be provided for easy separation of one test strip 10 from another.

To apply a test strip 10 on a piece to be painted, the backing 20 is peeled away to leave the inner surface 14 uncovered. The tape 12 is then pressed against a piece and held in place by the adhesive coating. The piece is then painted and cured in any desired manner. As the piece is painted, paint is also deposited on the outer surface of the tape 12 and the exposed area of the outer surface of the paint strip 18.

When the paint process is completed, the tape 12 is peeled away from the piece, and the paint strip 18 is removed from the tape 12. The tape 12 is discarded. Using suitable instruments such as a micrometer, the thickness of the paint, known as "film build", on the outer surface of the paint strip 18 can be easily measured. The paint strip 18 can be conveniently stored for future reference as needed.

The components of the test strip 10 are formed from materials which can withstand the painting and curing processes. For example, the tape 12 can be three (3) mil 219 style high temperature tape cut into desirable lengths. The paint strip 18 can be formed from five (5) mil Mylar.

The test strip 10 provides an economical means for testing film build on a painted plastic part such as an automotive fascia. Use of the test strip 10 does not require destruction of the piece in order to determine film build. After a test strip 10 is removed, the piece can be stripped, repainted and placed into use.

Figure 2:
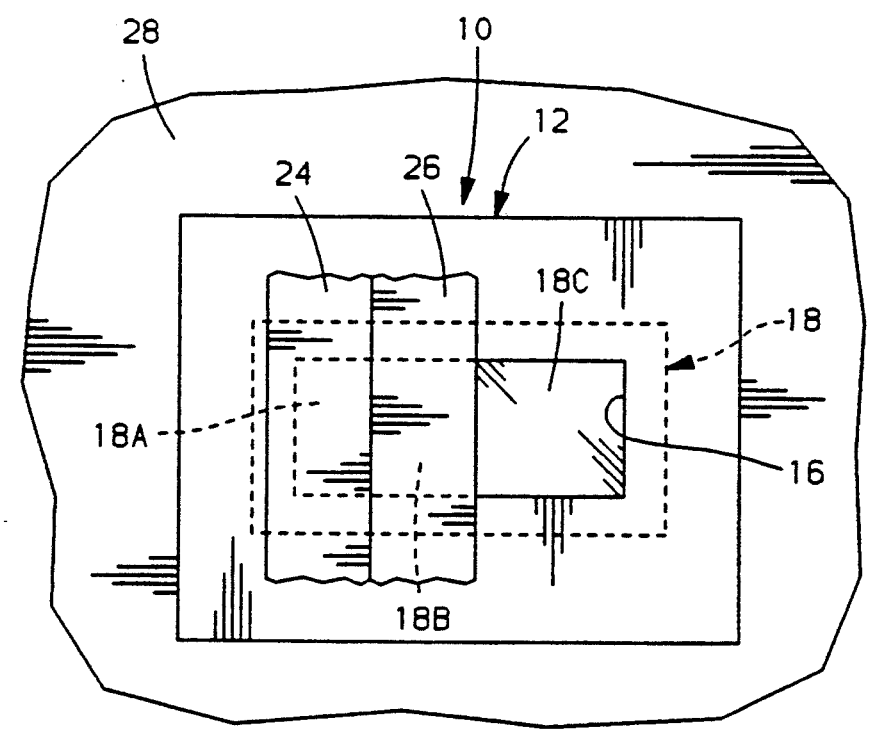
FIG. 2 is a view of the test strip of FIG. 1, mounted on a piece to be painted, including two pieces of tape covering portions of the paint strip which are used to form a film ladder on the paint strip.

The test strip 10 can also be used to determine film build of a process involving multiple painting operations. For example, a "film ladder" for a three-booth paint process can be created and analyzed using the test strip 10. As illustrated in FIG. 2, a first piece of covering tape 24 (such as masking tape) covers a first area 18A of the paint strip 18. A second piece of covering tape 26 (such as masking tape) is adhered to a second area 18B of the paint strip 18. A third area 18C of paint strip 18 is uncovered. The test strip 10 is mounted on a piece 28 such as an automotive fascia which is placed in a three-booth painting process.

After a first paint booth, tape 24 is removed. After a second paint booth, tape 26 is removed. After a third paint booth, the test strip 10 is peeled away from the piece 28. The paint strip 18 is separated from the tape 12 and the tape 12 is discarded.

The paint strip 18 has three areas 18A–18C of differing paint thickness. The third area 18C of the paint strip 18 received three applications of paint as it was uncovered during all three paint booths. The second area 18B of paint strip 18 was uncovered after the second paint booth, and thus received only one application of paint. The first area 18A of paint strip 18 was uncovered after the first paint booth, thereby receiving two applications of paint. Thus, a film ladder of three different builds is formed and can be analyzed to determine the film build occurring at each paint booth.

Although the present invention has been described with reference to a preferred embodiment, workers skilled in the art will recognize that changes may be made in form and detail without departing from the spirit and scope of the invention. Other variations and uses of the non-destructive test strip 10 are easily envisioned by an artisan.

The embodiments of the invention in which an exclusive property or privilege is claimed are defined as follows:

1. A test strip for measuring film build on a plastic piece to be painted, comprising:
   a) a desired length of tape having an adhesive coating on an inner surface and a window;
   b) a paint strip of sufficient area to cover the window secured to the tape by the adhesive coating; and
   c) a backing formed from material easily peeled from the adhesive coating.

2. The test strip specified in claim 1 including at least a first removable covering strip applied to an outer surface of the paint strip.

3. The test strip specified in claim 1 including:
   a) a first removable tape covering a first area of an outer surface of the paint strip; and
   b) a second removable tape covering a second area of an outer surface of the paint strip.

4. In combination, an unpainted automotive fascia and a non-destructive test strip for measuring paint thickness on the fascia after it has been painted, the test strip including:
   a) a desired length of tape having an adhesive coating on an inner surface and a window;
   b) a paint strip of sufficient area to cover the window secured to the tape by the adhesive coating; and
   c) a backing formed from material easily peeled from the adhesive coating.

5. The test strip specified in claim 4 including at least a first removable covering strip applied to an outer surface of the paint strip.

6. The test strip specified in claim 4 including:
   a) a first removable tape covering a first area of an outer surface of the paint strip; and
   b) a second removable tape covering a second area of an outer surface of the paint strip.

7. A method of determining film build on a plastic piece, comprising:
   a) cutting a window in a desired length of tape having an adhesive coating on an inner surface;
   b) securing a paint strip to the inner surface of the tape to cover the window;
   c) mounting the tape on the piece;
   d) simultaneously painting the piece and paint strip;
   e) removing the tape from the piece;
   f) separating the paint strip from the tape; and
   g) measuring film build on the paint strip.

8. The method specified in claim 7 including the step of applying at least one covering tape over the paint strip prior to painting the piece and paint strip.

* * * * *